United States Patent
Kadokura et al.

(10) Patent No.: US 6,930,177 B2
(45) Date of Patent: Aug. 16, 2005

(54) HIGH-PURITY LANTHANUM ISOPROXIDE AND A PROCESS FOR PRODUCING THE SAME

(75) Inventors: Hidekimi Kadokura, Tokyo (JP); Masamichi Matsumoto, Kumagaya (JP); Tadashi Ishii, Ogose-machi (JP); Yumie Okuhara, Yoshimi-machi (JP); Yoshinori Kuboshima, Mizuho-machi (JP); Hiroshi Matsumoto, Ageo (JP)

(73) Assignee: Kabushikikaisha Kojundokagaku Kenkyusho, Saitama (JP)

( * ) Notice: Subject to any disclaimer, the term of this patent is extended or adjusted under 35 U.S.C. 154(b) by 0 days.

(21) Appl. No.: 10/214,338

(22) Filed: Aug. 7, 2002

(65) Prior Publication Data

US 2003/0055228 A1 Mar. 20, 2003

(30) Foreign Application Priority Data

Sep. 20, 2001 (JP) ........................................ 2001-330005

(51) Int. Cl.$^7$ .................................................. C07F 5/00
(52) U.S. Cl. .......................... 534/15; 502/150; 502/160
(58) Field of Search ............................ 534/15; 502/150, 502/160; 585/485, 489; 423/244.1; 570/168, 169

(56) References Cited

U.S. PATENT DOCUMENTS 5,024,991 A * 6/1991 Tsunashima et al. ........ 505/512

OTHER PUBLICATIONS

Brown et al (1970), Inorganic Chemistry, vol. 9, No. 12, pp. 2783–2786.*
Brown et al (Inorganic Chemistry, 1970, vol. 9, No. 12, pp. 2783–2786).*

* cited by examiner

Primary Examiner—Dameron L. Jones
(74) Attorney, Agent, or Firm—Fattibene & Fattibene; Paul A. Fattibene; Arthur T. Fattibene

(57) ABSTRACT

The invention provides true La(OiPr)$_3$ preferable as a starting material for an asymmetric synthesis catalyst and a process for producing the same. In this process, anhydrous lanthanum chloride LaCl$_3$ is reacted with potassium isopropoxide K(OiPr) in a mixed solvent of isopropanol and toluene, then the isopropanol is distilled away to replace all the solvent by toluene, then the reaction solution is left, decanted and filtered to give a transparent filtrate, and the solvent is distilled away from the filtrate which is then vacuum-dried under heating, whereby high-purity La(OiPr)$_3$ is obtained in 77% yield. In this high-purity La(OiPr)$_3$, the La content is 97 to 103% of the theoretical content, impurity K is 0.3% or less, (Li+Na) is 0.01% or less, Cl is 0.2% or less, and the degree of association thereof is 5.5 to 6.5.

1 Claim, No Drawings

HIGH-PURITY LANTHANUM ISOPROXIDE AND A PROCESS FOR PRODUCING THE SAME

BACKGROUND OF THE INVENTION

1. Field of the Invention

This invention relates to high-purity lanthanum isopropoxide and a process for producing the same.

2. Description of the Related Art

The lanthanum isopropoxide $La(OiC_3H_7)_3$ (referred to hereinafter as $La(OiPr)_3$) is useful as a starting material for asymmetric synthetic catalyst or as a starting material for fine particles or film containing lanthanum oxide. Shibasaki et al. found that a La—Na-BINOL catalyst obtained by reacting $La(OiPr)_3$ with optically active binaphthol [referred to hereinafter as BINOL] and sodium tertiary butoxide is useful for asymmetric Michael reaction (JP-A 8-291178). Similarly, a La—K-BINOL catalyst is useful for asymmetric hydrophoshonylation (JP-A 8-325281) while a La—Li-BINOL catalyst is useful for asymmetric Mannich reaction (JP-A 2000-72727). Further, a La-BINOL catalyst is useful for asymmetric epoxidation reaction (JP-A 10-120668).

It is empirically found that the catalytic performance thereof is influenced by the producing process and physical properties of $La(OiPr)_3$, but the cause therefor is not elucidated. Accordingly, there is the need for further excellent $La(OiPr)_3$ as a starting material for the catalyst giving higher reproducibility.

Known processes for producing $La(OiPr)_3$ include:
(1) $LaCl_3+3Na(OiPr)=La(OiPr)_3+3NaCl$
(2) $LaCl_3.3iPrOH+3nBuLi=La(OiPr)_3.3LiCl+nBuH$
(3) $La(OOCR)_3+3Na(OiPr)=La(OiPr)_3+3Na(OOCR)$
(4) $La+3iPrOH=La(OiPr)_3+3/2H_2$ In the process (1), $La(OiPr)_3$ was obtained by reacting the starting materials in equivalent amounts in boiling isopropanol (S. N. Misra, T. N. Misra, R. N. Kapoor and R. C. Mehrotra, Chemistry & Industry, 120 (1963)). The literature does not refer to the analytical contents of impurities, alkali metals and Cl, in the synthesized $La(OiPr)_3$. There are few literatures describing the specific analytical contents of impurities, alkali metals and Cl, and only JP-A 6-1737 discloses the contents of Na and Cl.

In the process (2), A. Lebrun et al. in Tetrahedron Letters, vol. 32, 2355 (1991) describe that LiCl coordinates to $La(OiPr)_3$ and it is hard to be purified.

JP-B 62-6694 concerning the process (3) does not describe the content of La or the amount of impurity Na.

In the direct method (4), there are no impurities such as alkali metals and Cl. L. M. Brown and K. S. Mazdiyasni in Inorg. Chem. Vol. 9, 2783 (1970) describe that $La(OiPr)_3$ can be synthesized by reacting La with isopropanol directly in the presence of a $HgCl_2$ catalyst, but there is no specific description such as sublimation data, La content, and yield, although there is a description of data on isopropoxide with 13 other lanthanoids. The present inventors confirmed that the La content is often higher than the theoretical content, possibly because compounds having La—O—La bonds (e.g. $La_xO_y(OiPr)_z$) have been formed. The La content in Comparative Example 4 was as high as 112% based on the theoretical content.

When the oxide film on the surface of the La metal is strong, the induction time is prolonged, and the reaction time is thus prolonged, and as a result, the product may be easily deteriorated. Further, the catalyst used is a Hg salt, so the prior art process is not preferable as an industrial process.

JP-A 6-1737 describes that when $Na(OiPr)$ is charged in excess, the product $La(OiPr)_3$ cannot be separated even by repeated re-crystallization from toluene, possibly because the excess starting material acts together with the product to form a complex. It is therefore described therein that because $LaCl_3$ is insoluble in toluene, use of the other starting material $LaCl_3$ in slight excess is very effective in eliminating the Na content and in reducing the reaction time. In this case, Na is absent, but Cl remains. In such case, Cl is estimated to be contained in compounds such as $La_6(OiPr)_{17}Cl$. This is the present inventors' estimation because R. A. Andersen et al. in Inorg. Chem. Vol. 17, 1962 (1978) synthesized and identified $Nd_6(OiPr)_{17}Cl$.

Further, it is noted that $Y(OiPr)_3$ is often identified with $Y_5O(OiPr)_{13}$ or contains $Y_5O(OiPr)_{13}$ depending on the synthesis process, synthesis conditions and purification method, and O. Poncelet et al. in Inorg. Chem. Vol. 28, 263 (1989) synthesized and identified $Y_5O(OiPr)_{13}$. This can also apply to $Ln(OiPr)_3$ wherein Ln is a lanthanoid, and it is noted that the product partially contains $Ln_5O(OiPr)_{13}$.

There is no report on the $La(OiPr)_3$ system, but when the La content is higher than the theoretical content of 43.9 wt-%, the product is assumed to contain compounds such as $La_5O(OiPr)_{13}$. This compound contains La—O—La bonds besides La—O—iPr. That is, pure $La(OiPr)_3$ must be an aggregate of $La(OiPr)_3$, which consists of a "n"-mer represented by $[La(OiPr)_3]_n$. The pure compound must not contain the La—O—La oxide. In high-purity $La(OiPr)_3$, the amount of alkali metals, Cl, and La—O—La oxide must be very low. However, there are few literatures on measurement of "n" or structural analysis of the aggregate, and if any, there are doubts about reliability. The present inventors estimated that the major reason therefor is that the substance measured was not real $[La(OiPr)_3]_n$.

N. I. Kozlova et al. in Koord. Khim. Vol. 8, 639 (1982) had concluded that because in mass spectrometry of $La(OiPr)_3$ crystals obtained by direct synthesis method in the production process (4), the strongest spectrum at the maximum m/Z was attributable to $La_5(OiPr)_{11}O^+$, the product was a pentamer, that is, $[La(OiPr)_3]_5$.

However, it seems that this substance was not the real $La(OiPr)_3$ because its melting point described therein was 120 to 128° C. The present inventors estimated that this substance is $La_5O(OiPr)_{13}.niPrOH$ (n=2). This is because the low melting point suggests coordination of isopropanol thereto and the La content suits well with the theoretical value of 43.5% for the coordinated compound.

On one hand, S. N. Misra, T. N. Misra, R. N. Kapoor and R. C. Mehrotra in Chemistry & Industry (London) 120 (1963) had reported that $La(OiPr)_3$ sublimed at 250 to 300° C./0.1 Torr, and occurred as a monomer in benzene. According to R. C. Mehrotra and J. M. Batwara in Inorg. Chem. Vol. 9, 2505 (1970), the lowest sublimation temperature of $La(OiPr)_3$ was 250 to 280° C./0.01 Torr. However, if this substance is a monomer, the substance should sublimed easily at 200° C. or less because of its low molecular weight, so the reference thereof to as a monomer is not reliable.

D. C. Bradley, R. C. Mehrotra and D. P. Gaur in "Metal Alkoxides" (Academic Press, 1978) p. 104 have estimated the structure of lanthanoid isopropoxide, assuming that it occurs inherently as a tetramer. However, lanthanoid elements are significantly different from each other in ionic radius and coordination number, so the properties of $La(OiPr)_3$ can be different from those of other counterparts. They have not measured or discussed $La(OiPr)_3$. As described above, the degree of association and structure of the real La $(OiPr)_3$ have not been definitely determined. In the lanthanoid group, $La(OiPr)_3$ is the most indefinite compound.

There are few literatures on synthesis of La(OiPr)$_3$ where the La content was analyzed. In JP-A 6-1737, the La content in Example 1 is 43.7 wt-% which is certainly near to the theoretical value, but Na content is 2.3 wt-%, so when OiPr in Na(OiPr) is subtracted therefrom (that is, OiPr=54.1–(59/23)×2.3=48.2 wt-%), OiPr of 48.2 wt-% is bound to La. That is, OiPr mole/La mole=(48.2/59)/(43.7/138.9)=2.60, which is considerably lower than the theoretical value of 3. This value is significantly deviated from the theoretical value, even assuming that the analysis accuracy of La is ±2%. This is probably because compounds having La—O—La bonds are contained as impurities in a considerable amount.

On the other hand, in Example 4 wherein Na is absent and Cl is 0.4 wt-%, Cl mole/La mole=(0.4/35.45)/(44.1/138.9)=0.04, indicating that there are 4% La—Cl bonds.

In the Examples and Comparative Examples in JP-A 6-1737, La(OiPr)$_3$ of highest purity contains La, 44.1%; Na, not described; and Cl, 0.4%. The content of Na (not described) assumed from analysis accuracy is that Na<about 0.1%. There were no other literatures describing the analytical contents of the 3 elements La, Na and Cl. That is, La(OiPr)$_3$ of highest purity in the prior art contains La, 44.1%; Na<0.1%; and Cl, 0.4%.

There are no literatures referring to the behavior of synthesis reaction of La(OiPr)$_3$ by using K(OiPr) in place of Na(OiPr) or to the La content in the product and the amount of K and Cl impurities.

SUMMARY OF THE INVENTION

La(OiPr)$_3$ with a higher La content than the theoretical value, that is, La(OiPr)$_3$ containing La—O—La compounds and much impurity such as Na and Cl, is considered to be not an aggregate represented by simple [La(OiPr)$_3$]$_n$. That is, La(OiPr)$_3$ is considered to be coordinated or mixed with compounds such as La$_5$O(OiPr)$_{13}$, Na(OiPr) and La$_6$(OiPr)$_{17}$Cl. Accordingly, it is estimated that such La(OiPr)$_3$ does not normally react with BINOL, resulting in a reduction in the performance of the resulting asymmetric synthesis catalyst. Accordingly, the present inventors estimated that La(OiPr)$_3$ that is a starting material for the asymmetric synthesis catalyst enabling reaction at a high yield and at a high excess enantiomer ratio with high reproducibility is preferably the one whose La content is substantially the theoretical value and whose Na, Li, K and Cl contents are as low as possible. The phrase "La content is substantially the theoretical value" means that in consideration of the accuracy of the analytical value, the La content is in the range of 97 to 103% of the theoretical value (i.e. 43.9%) Accordingly, the object of this invention is to provide high-purity La(OiPr)$_3$ having such physical properties and a process for producing the same.

When K(OiPr) was used in place of Na(OiPr) as a reactant with LaCl$_3$, the present inventors found the following phenomenon to complete the invention. That is, the reaction time can be reduced by half, impurities such as alkali metals and Cl can be reduced very low, and La(OiPr)$_3$ whose La content agrees with the theoretical value can be produced with good reproducibility, and by replacing the solvent by toluene, byproducts are solidified as a lower layer in the form of jelly, so the La(OiPr)$_3$ solution can be easily recovered.

This invention relates to high-purity lanthanum isopropoxide wherein the La content is 97 to 103% of the theoretical value, impurity K is 0.3% or less, (Li+Na) is 0.01% or less, and Cl is 0.2% or less.

Further, this invention relates to the high-purity lanthanum isopropoxide, wherein the degree of association thereof obtained in molecular weight measurement by cryoscopy with benzene is 5.5 to 6.5.

Further, this invention relates to aprocess for producing high-purity lanthanum isopropoxide, which comprises reacting anhydrous lanthanum chloride LaCl$_3$ with potassium isopropoxide K(OiPr) in a mixed solvent of isopropanol and toluene, then distilling the isopropanol away to replace all the solvent by the toluene, leaving the reaction solution, decanting and filtering it to give a transparent filtrate, distilling the solvent away from the filtrate, and heating and vacuum-drying thereof.

DETAILED DESCRIPTION OF THE PREFERRED EMBODIMENTS

LaCl$_3$ used in this invention is anhydrous LaCl$_3$ which is preferably free of LaOCl and LaCl$_3$.nH$_2$O as impurities. Further, LaCl$_3$ is preferably a powder as fine as possible to increase the reaction rate. K(OiPr) is obtained easily by charging a mass of metal K into dehydrated isopropanol and reacting them at room temperature to boiling point. The synthesized K(OiPr) may be used directly as the isopropanol solution or as a conc. K(OiPr) solution after a part of the isopropanol is evaporated and distilled away.

The reaction solvent in this invention is a mixed solvent of isopropanol and toluene. As can be seen from the Comparative Examples, pure isopropanol is not preferable because side reactions are increased and the yield is lowered. Pure toluene is not preferable either because the reaction rate is decreased. The solvents, isopropanol and toluene, should be mixed such that both are substantially present, and the proportion of the two solvents is preferably in the range of about 3:7 to 7:3.

LaCl$_3$ powder is charged in one portion to a solution of K(OiPr) in a mixed solvent of isopropanol and toluene and reacted for 5 to 50 hours under reflux and stirring. The molar ratio of K(OiPr)$_3$/LaCl$_3$ charged is preferably about 3 i.e. the equivalent. As the reaction proceeds, the LaCl$_3$ powder disappears to form a suspension of finer particles. The La(OiPr)$_3$ thus formed has been dissolved in the mixed solvent of isopropanol and toluene.

The reaction solution, when left by terminating stirring during the reaction, is easily separated into a colorless and transparent supernatant layer and a lower white suspension. The supernatant layer is sampled and hydrolyzed with a 10-fold volume of water, and the pH value of the aqueous phase is measured, whereby the approximate reaction end point can be known.

When the pH value reduced to about 10.5 or less, the degree of conversion can be calculated to be 99.8% or more, so the process advances to the next replacement step.

In the step of replacing the solvent, all the isopropanol in the reaction solution is replaced by toluene. The majority of the formed La(OiPr)$_3$ is dissolved in toluene, while byproducts KCl and La$_x$(OiPr)$_y$Cl form a gel which when left, is solidified as a lower layer in the form of jelly. Accordingly, separation of the byproducts is made easily, to increase the purity of the supernatant toluene layer.

The present inventors found this phenomenon for the first time and apply it to this invention.

Without replacement by toluene, unreacted K(OiPr) and byproduct La$_x$(OiPr)$_y$Cl are also dissolved in the solvent and hardly separated by filtration, to cause a reduction in the purity of La(OiPr)$_3$.

There are various methods of replacing the solvent. By way of example, the reaction solution is heated and stirred whereby a part of the mixed solvent is distilled away, then toluene is added in the same volume of the solvent distilled away, the reaction solution is heated and stirred again, whereby the solvent in almost the same volume of toluene added is distilled away. This procedure is repeated several times, whereby all the solvent can be replaced by toluene. Because a mixed solvent of 58 wt-% isopropanol and 42 wt-% toluene undergoes azeotropic distillation at 80.6° C., replacement of the solvent by toluene is easy. The replacement is complete if the replacement procedure is repeated one more time when the distillation temperature reaches the boiling point of toluene.

After replacement by toluene, the reaction solution is heated under stirring, left and cooled to room temperature. When left for 0.5 to 12 hours, the reaction solution is separated into 60 to 80 vol-% colorless and transparent supernatant layer and a lower white jelly layer containing precipitated particles. This supernatant layer is transferred by decantation to a filter, and fine particles contained therein in a very small amount are filtered off. The "decantation" refers to the general operation of separating the supernatant layer from the white jelly layer, and is carried out by a method of inclining the reaction vessel or by a method of sucking the supernatant layer via a tube inserted therein. The white jelly layer becomes jelly that is so strong as not to be mixed in the supernatant layer during decantation, thus making the separation very easy. When the contents are not left, the jelly is not formed and the efficiency of filtration is lowered, thus permitting a larger amount of impurities to be mixed therewith, so elimination of the step of leaving the contents is not preferable.

The present inventors found for the first time that the phenomenon of clear separation of the supernatant layer from the white jelly layer and formation of the strong jelly layer occurs only when K(OiPr) is used, and they applied this phenomenon to the invention. This phenomenon is not described in the preceding literatures. Na(OiPr) does not produce a strong jelly layer.

When the white jelly layer in Example 1 was recovered, dried in vacuo under heating and analyzed, the following contents were revealed: K, 40%; Cl>30%; and La, 4.0%, suggesting that the white jelly layer is composed mainly of KCl and $La_x(OiPr)_yCl_z$. Accordingly, formation of the white jelly layer leads to a reduction in KCl and $La_x(OiPr)_yCl_z$ in the supernatant layer, thus resulting in a reduction in K and Cl in the product $La(OiPr)_3$.

The filter paper used in the filtration step is preferably Toyo Roshi paper No. 131 (retention particle diameter, 3 μm) or a paper of finer pores, and filtration can be effected almost instantaneously.

Then, the filtrate is heated at ordinary pressure or under reduced pressure, whereby the toluene solvent is distilled away, and finally the sample is dried under vacuum at 1 Torr at 100 to 120° C. for 1 to 24 hours, to give white $La(OiPr)_3$.

The product $La(OiPr)_3$ is still dissolved in the toluene in the initially formed white jelly layer, and this $La(OiPr)_3$ can be recovered as a second crop. When toluene is added to the jelly layer which is then heated under stirring, the jelly layer is re-dispersed in the solution. Then, the contents are left and separated into a supernatant toluene layer and a lower white jelly layer. From this supernatant toluene layer, the second crop may be recovered in the same manner as for the first crop. The resultant $La(OiPr)_3$, similar to the first crop, is of high purity. By recovering the second crop, the yield is improved by 10 to 20%.

The recovered $La(OiPr)_3$ was analyzed. In this analysis, $La(OiPr)_3$ was decomposed with conc. nitric acid, evaporated into dryness, dissolved in nitric acid, diluted, and quantitatively analyzed by ICP-AES and atomic absorption spectrometry, to determine the contents of La, K, Na and Li therein. The accuracy of the La content was about ±2%. Cl was determined by potential difference titration after decomposition with dilute sulfuric acid.

The La content in the $La(OiPr)_3$ of the invention is in the range of 97 to 103% of the theoretical content, and K<0.3%, (Li+Na)<0.01%, and Cl<0.2%. As a result, even if every K is assumed to be present in the form of K(OiPr), K(OiPr)/$La(OiPr)_3$<(0.3/39.1)/(43.9/138.9)=0.024, that is, the product comprises 97.6 mol-% $La(OiPr)_3$, thus indicating high purity.

For use where $La(OiPr)_3$ can be used directly in the form of the toluene solution, the solution can be used without distilling the toluene away.

To know the degree of association of the $La(OiPr)_3$ of the invention, the molecular weight thereof was measured by cryoscopy with benzene. The degree of association is a value obtained by dividing the obtained molecular weight by 316.18 that is the formula weight of $La(OiPr)_3$. 1.8185 g $La(OiPr)_3$ obtained in Example 1 was dissolved in 20.8 g benzene, and the freezing point depression as determined by cryoscopy was 0.237° C. From this result, the molecular weight is 1890. Accordingly, the degree of association thereof is 1890/316.18=5.98. Further, 3.0886 g $La(OiPr)_3$ synthesized in a 8-fold scale relative to Example 1 was dissolved in 20.0 g benzene and the freezing point depression as determined by cryoscopy was 0.396° C. From this result, the molecular weight is 1997. Accordingly, the degree of association thereof is 1997/316.18=6.32.

In consideration of the results and experimental accuracy in these 2 experiments, the degree of association thereof is in the range of 5.5 to 6.5.

Accordingly, it is concluded that the $La(OiPr)_3$ of the invention is composed mainly of a hexamer of $La(OiPr)_3$, which is represented by $[La(OiPr)_3]_6$.

The solubility of the $La(OiPr)_3$ of the invention in a solvent was examined. The result indicated that the solubility thereof in 1 L solvent was 450 g in toluene, 390 g in hexane, 500 g in THF or 60 g in isopropanol. This product was characterized by being dissolved very well in toluene, hexane or THF, but being sparingly dissolved in isopropanol.

The melting point and volatility of the $La(OiPr)_3$ of the invention were examined. There was no melting point between room temperature and 250° C. Sublimation thereof was attempted at 0.5 Torr, and partial sublimation occurred at 250° C., but pyrolysis was initiated, and the majority thereof was not sublimed.

The asymmetric synthesis catalyst produced by using the $La(OiPr)_3$ of the invention can give a higher yield and a higher excess enantiomer ratio with good reproducibility in asymmetric synthesis reaction. On the other hand, $La(OiPr)_3$ wherein the La content may be significantly different from the theoretical value, which was produced from e.g. a La metal by another process, exhibits varying catalytic performance.

Hereinafter, this invention is described in more detail by reference to the Examples.

EXAMPLE 1

A 100-ml three-necked flask equipped with a stirrer, a reflux condenser and an inlet was evacuated and flushed with argon, and charged with 50 ml dehydrated isopropanol and then with 3.0 g (77 mmol) K metal mass. The mixture was heated for 1 hour at an increasing temperature from room temperature to finally 50° C., whereby all K was reacted to form K(OiPr). Then, 22 ml isopropanol was distilled away at ordinary pressure, and the reaction solution was charged with 33 ml dehydrated toluene.

The proportion of the mixed solvent was isopropanol:toluene=22 ml:33 ml=0.4:0.6. 6.3 g (26 mmol) of anhydrous $LaCl_3$ was introduced into it, and the resulting suspension was heated under stirring and refluxed for 24 hours. Thereafter, the reaction solution was left and cooled, whereby the solution was separated into a transparent supernatant layer and a white suspension layer. 0.5 ml of the supernatant layer was sampled and hydrolyzed with 5 ml deionized water, and the pH value as determined for its aqueous phase was 10.46, suggesting about 99.8% degree of conversion.

Then, 28 ml of the solvent was distilled away at ordinary pressure, then 28 ml toluene was added thereto, 28 ml of the second solvent was distilled away, 28 ml toluene was added thereto, 28 ml of the third solvent was distilled away, 28 ml toluene was added thereto, and the solution was heated and stirred for 0.5 hour, left and cooled.

After 1 hour, a colorless and transparent supernatant layer and a white jelly layer containing precipitated particles were formed. The supernatant layer was recovered by decantation and then filtered through Toyo Roshi filter paper No. 131, to give 48 ml colorless and transparent filtrate. From this filtrate, the solvent was distilled away by heating under reduced pressure, and the remaining solution was finally vacuum-dried at 1 Torr, at 100° C. for 1 hour to give 5.3 g white solids.

The first crop thus obtained was comprised of 17 mmol $La(OiPr)_3$, and the yield was 65%. The analysis results of the first crop was that the La content was 43.1% (98.2% of the theoretical value); K, 0.15%; Cl, 0.17%; Li<10 ppm; Na<10 ppm; Ca, 20 ppm; Al<8 ppm; Cr<3 ppm; Cu<3 ppm; Fe<3 ppm; Mg<1 ppm; Mn<1 ppm; and Zn, 5 ppm, indicating high purity.

50 ml toluene was added to the above white jelly layer which was then heated under stirring and left, whereby the suspension was separated into a colorless and transparent supernatant layer and a white jelly layer in the same manner as in the first procedure. The same procedure as the first one was repeated to give 1.0 g second crop $La(OiPr)_3$. The product was comprised of 3 mmol $La(OiPr)_3$, and the yield was 12%. The analysis results of the second crop indicated that the La content was 44.0%; K, 0.18%; and Cl, 0.19%.

Since precipitated particles were present in the lowermost part of the white jelly layer, about 50% (5.5 g) of the white semitransparent jelly layer excluding the precipitated particles was recovered and the solvent was distilled away by heating under reduced pressure, and finally the contents were vacuum-dried at 1 Torr, at 100° C. for 1 hour, to give 2.0 g white solids. The analysis result of the white solids indicated that La was 4.0%; K, 40%; Cl>30%. To know the amount of the base therein, the white solids were hydrolyzed and measured for its pH, and as a result, the amount of K(OiPr) was negligible. That is, the amount of KCl in the precipitated particles in the white jelly layer is about 2.7 g, suggesting that the jelly is made mainly of KCl and a small amount of $La(OiPr)_3$ or $La_6(OiPr)_{17}Cl$.

EXAMPLE 2

The same operation as in Example 1 was conducted except that the reaction time was 36 hours in place of 24 hours in Example 1. The amount of the first crop $La(OiPr)_3$ obtained from a filtrate of the supernatant layer was 4.4 g, and the yield was 54%. The analysis result of the $La(OiPr)_3$ indicated that La was 44.7%; K, 0.16%; (Li+Na)<0.01%; and Cl, 0.04%. This product was high-purity $La(OiPr)_3$, but its yield was lower than in Example 1. The reason for this is possibly that the reaction time is too long, thus increasing side reactions.

Comparative Example 1

The same operation as in Example 1 was conducted except that the solution in pure isopropanol was used in place of the solution in the mixed solvent in Example 1. The amount of the first crop $La(OiPr)_3$ obtained from the filtrate was 3.4 g, and the yield was 42%. The analysis result of the $La(OiPr)_3$ indicated that La was 45.2%; K, 0.40%; (Li+Na) <0.01%; and Cl, 0.02%. As compared with Example 1, the yield was low and much K was present.

Comparative Example 2

The same operation as in Example 1 was conducted except that the replacement of the solvent by toluene was not conducted. The lower layer was soft precipitates and not solidified as jelly. Filtration of the supernatant layer was significantly slower than in Example 1. The amount of the first crop $La(OiPr)_3$ obtained from the filtrate was 5.4 g, and the yield was 67%. The analysis result of the $La(OiPr)_3$ indicated that La was 43.4%; K, 0.80%; (Li+Na)<0.01%; and Cl, 0.27%, revealing that the product was not high-purity $La(OiPr)_3$.

Comparative Example 3

The same operation as in Example 1 was conducted except that 1.8 g (78 mmol) Na was used in place of K. No white jelly layer was formed, and a soft precipitated layer was formed. The amount of the first crop $La(OiPr)_3$ was 4.6 g, and the yield was 57%. The analysis result of the $La(OiPr)_3$ indicated that La was 44.0%; Na, 1.97%; (Li+K) <0.01%; and Cl, 0.28%, revealing that the product was not high-purity $La(OiPr)_3$.

Comparative Example 4

A 100-ml three-necked flask equipped with a stirrer, a reflux condenser and an inlet was evacuated and flushed with argon, charged with 40 ml dehydrated isopropanol and 40 ml toluene, then with 3.0 g cut La piece, and with 0.03 g mercury chloride ($HgCl_2$). The mixture was heated and refluxed for 24 hours. For about initial 10 hours, the reaction was not initiated. Thereafter, the reaction was initiated, and a byproduct hydrogen gas was generated and the majority of La was reacted. After cooling, the reaction solution was filtered as such, and the solvent was distilled away by heating under reduced pressure. Then, 55 ml toluene was added to the dried residues which were then heated under stirring, left and cooled to be separated into a transparent supernatant layer and a lower white suspension layer. The transparent layer was recovered by decantation, the toluene was distilled away by heating under reduced pressure, and the remaining contents were vacuum-dried under heating to give 2.9 g pale yellow solids. The yield of $La(OiPr)_3$ was 42%.

The analysis result of the $La(OiPr)_3$ indicated that the La content was 49.2%, (Na+K+Li)<0.01%; and Cl<0.1%. Because the La content in this product is as high as 112% of the theoretical content, La—O—La compounds are contained in a considerable amount. The degree of association measured for this product was 8.1. It is estimated that La—O—La-containing compounds such as $La_xO_y(OiPr)_z$ insoluble in toluene are contained in a large amount in the lower white suspension layer.

Separately, 3 cut La pieces from different lots were subjected to the same reaction as above. Depending on lots, the time necessary for initiating the reaction was significantly varied, and the time necessary for attaining a certain stage of the reaction, estimated by monitoring generated gas, was significantly varied from 7 to 32 hours. The yield was varied from 23 to 51%, and the La content in the resultant $La(OiPr)_3$ was varied from 45.4 to 51.7%.

Real $La(OiPr)_3$ preferable as a starting material for an asymmetric synthesis catalyst can be produced with good reproducibility.

What is claimed is:

1. A process for producing high-purity lanthanum isopropoxide, which comprises reacting anhydrous lanthanum chloride $LaCl_3$ with potassium isopropoxide $K(OiPr)$ in a mixed solvent of isopropanol and toluene, then distilling the isopropanol away to replace all the solvent by the toluene, leaving the reaction solution, decanting and filtering it to give a transparent filtrate, distilling the solvent away from the filtrate, and heating and vacuum-drying thereof.

* * * * *